United States Patent [19]

Miura et al.

[11] 4,010,072

[45] Mar. 1, 1977

[54] PROCESS FOR PREPARING L-TARTARIC ACID

[75] Inventors: Yuichi Miura, Tokuyama; Kiyohiko Yutani, Kudamatsu; Yusuke Izumi, Shinnanyo, all of Japan

[73] Assignee: Tokuyama Soda Kabushiki Kaisha, Japan

[22] Filed: Feb. 5, 1976

[21] Appl. No.: 655,422

[30] Foreign Application Priority Data

Feb. 14, 1975 Japan .............................. 50-17973

[52] U.S. Cl. .................................. 195/30; 195/62; 195/66 R
[51] Int. Cl.² .......................................... C12D 1/02
[58] Field of Search ......................... 195/30, 62, 66

[56] References Cited

OTHER PUBLICATIONS

Martin et al. Journal of Bacteriology vol. 70 pp. 405–414 (1955).

*Primary Examiner*—Alvin E. Tanenholtz
*Attorney, Agent, or Firm*—Fitzpatrick, Cella, Harper & Scinto

[57] ABSTRACT

A process for preparing L-tartaric acid, which comprises contacting a microorganism of the genus Nocardia having the ability to produce an enzyme which cleaves and hydrolyzes the epoxy ring of cis-epoxysuccinic acid, or an enzyme isolated therefrom, with cis-epoxysuccinic acid or its derivatives in an aqueous medium, and recovering the resulting L-tartaric acid.

15 Claims, 5 Drawing Figures

Fig. 1

2ND SEPHADEX G-200 GEL FILTRATION

Figure 4:
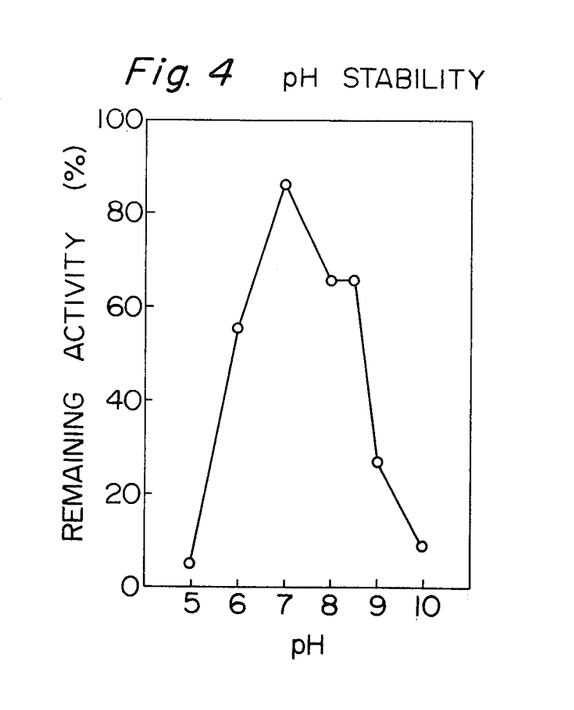

Fig. 4 pH STABILITY

Figure 5:
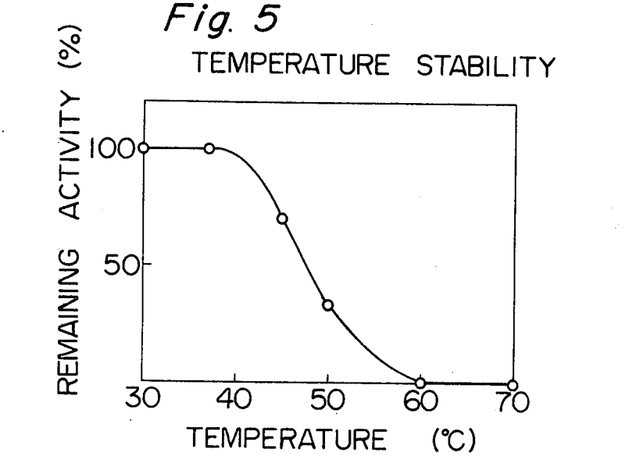

Fig. 5 TEMPERATURE STABILITY

PROCESS FOR PREPARING L-TARTARIC ACID

This invention relates to a process for preparing L-tartaric acid, the same type as naturally occurring tartaric acid, from inexpensive and readily available cis-epoxysuccinic acid or its derivatives by an enzymatic technique with commercial advantage. More specifically, the invention relates to a process for preparing L-tartaric acid which comprises contacting a microorganism belonging to the genus Nocardia and having the ability to produce an enzyme which hydrolyzes the epoxy ring of cis-epoxysuccinic acid, or an enzyme isolated from said microorganism with cis-epoxysuccinic acid or its derivatives in an aqueous medium, and recovering the resulting L-tartaric acid.

L-tartaric acid, as used in the present application, is a term denoting dextrorotatory (+) tartaric acid which is natural tartaric acid.

Heretofore, L-tartaric acid has been produced by extracting techniques using tartar in wine lees as a raw material. The supply of the raw material has therefore been unstable and restricted, and it has been desired to develop a process which can afford L-tartaric acid from an inexpensive and readily available raw material. In an attempt to meet this demand, methods for synthesizing tartaric acid from maleic acid as a raw material have been developed. The tartaric acid obtained by such methods, however, is a racemic form (DL-form). The DL-form has a defect of exceedingly lower solubility than L-form, and this defect has limited its utilization in many ways. It is very disadvantageous, on the other hand, from the viewpoint of operation and cost to convert the DL-form to an L-form by a complex and disadvantageous optically resolving technique and racemizing technique.

Some suggestions have already been made to produce tartaric acid by a fermentation technique or a technique utilizing microorganisms. For example, U.S. Pat. No. 2,947,665 discloses that meso-tartaric acid can be produced by hydrolyzing trans-epoxysuccinic acid by a technique utilizing a microorganism. However, the U.S. patent fails to show the production of L-tartaric acid and any technique using microorganisms for the preparation of L-tartaric acid from cis-epoxysuccinic acid. Very recently, a technique for producing L-tartaric acid from cis-epoxysuccinic acid by a tehcnique utilizing microorganisms was suggested (Japanese Laid-Open Patent Publications Nos. 140683/75 and 140684/75 and German OLS 2517941). These patents disclose that microorganisms belonging to the genus Achromobacter or the genus Alcaligenes have the ability to produce an enzyme which is useful for enzymatically converting cis-epoxysuccinic acid to L-tartaric acid (termed "d-tartaric acid" in these patents). However, the patents fail to show anything about microorganisms which belong to the genus Nocardia, a quite different genus.

We have discovered the existence of microorganisms of the genus Nocardia which have the ability to produce an enzyme that can enzymatically convert inexpensive and readily available cis-epoxysuccinic acid to L-tartaric acid with superior activity. We have also found that the enzyme which is produced by the microorganisms of the genus Nocardia, for example, *Nocardia tartaricans* nov. sp., and can convert cis-epoxysuccinic acid to L-tartaric acid by hydrolyzing its epoxy ring (which will be referred to as cis-epxoysuccinate hydrolase) is completely different from the enzymes described in the above-cited patents in some of their properties such as the molecular weight, optimum pH or optimum temperature.

The development of the process of this invention has made it possible to provide L-tartaric acid at lower cost and with greater availability, and therefore, is an important contribution to the field of technology to which the present invention pertains.

Accordingly, it is an object of this invention to provide a process for preparing L-tartaric acid, the same type as natural tartaric acid, with commerical advantage.

Another object of this invention is to provide microorganisms and enzymes produced thereby for utilization in achieving the aforesaid object, and to provide a process which contributes further to the technology of preparing L-tartaric acid.

The above and other objects of this invention along with its advantages will become more apparent from the following description.

The cis-epoxysuccinic acid or its derivatives used in the performance of the process of this invention can be easily obtained, for example, by epoxidizing maleic anhydride, maleic acid or a derivative of any of these with hydrogen peroxide. Examples of the derivatives of cis-epoxysuccinic acid are inorganic salts such as sodium, potassium, calcium and ammonium salts of said acid; organic salts such as primary, secondary and tertiary aliphatic amine, aromatic amine, pyridine and quinoline salts of said acid; and esters or amides such as those formed between said acid and aliphatic alcohols or aromatic alcohols or primary of secondary aliphatic or aromatic amines. Any derivatives can be used which are soluble in the aqueous medium and do not adversely affect the ability of the cis-epoxysuccinate hydrolase to hydrolyze the epoxy ring of cis-epoxysuccinic acid. The cis-epoxysuccinic acid or its derivatives may be in the form of crystals or the reaction mixture as obtained by a synthetic process. However, the presence of impurities in amounts which will retard the reaction, such as too much hydrogen peroxide, is not desirable.

The concentration of the substrate in the process of this invention can be varied over a wide range, usually from 0.1% by weight as initially charged to very high concentrations. When cis-epoxysuccinic acid or its derivatives is caused to be present at the time of growing microbial cells in culture media, the growth of the cells tends to be inhibited by too high a concentration of cis-epoxysuccinic acid. Preferably, therefore, the concentration of the cis-epoxysuccinic acid or its derivatives should be adjusted, for example, to not more than about 10%, preferably not more than 5% by weight. Higher concentrations can be employed when the microorganism in accordance with this invention or an L-tartaric acid-forming enzyme isolated therefrom is contacted with cis-epoxysuccinic acid or its derivatives in a system for hydrolyzing the cis-epoxysuccinic acid or its derivatives which is free from the growth of microbial cells.

One preferred species of microorganisms belonging to the genus Nocardia having the ability to produce cis-epoxysuccinate hydrolase is *Nocardia tartaricans* nov. sp. separated from nature. Typical strains of the *Nocardia tartaricans* nov. sp. are deposited in Fermentation Research Institute, Agency of Science and Technology, Japan, and American Type Culture Collection, U.S.A. The characteristics of these strains are described below.

Description of Nocardia tartaricans nov. sp.

I. Strain ES1-T (FERM P NO. 2882; ATCC 31191)

A. Morphological characteristics

Rods: 0.8 – 1.0$\mu$ by 5 – 30$\mu$ in young cultures, 0.8 – 1.0$\mu$ by 1 – 5$\mu$ in older cultures; in young cultures, mycelium-like development, branching, bending are observed; in older cultures, small rods to coccoids; aerial mycelium is not formed on any tested agar slant; non-motile; not acid-fast; Gram-positive; spore is not formed B. Cultural characteristics
1. Nutrient agar colonies: circular, capitate, smooth, entire, opaque, glistening, yellowish-orange to reddish orange
2. Glucose-peptone agar colonies: circular, umbonate, smooth, undulate, opaque, dull, yellowish orange
3. Glycerol-asparagine agar colonies: rhizoid, umbonate, opaque, glistning, pale orange
4. Nutrient broth: slightly turbid, pellicle, sediment
5. Gelatin stab: good growth at surface, no liquefaction
6. Nutrient agar slant: growth abundant, spreading, glistening, butyrous, pale yellowish brown at first, becoming yellowish orange and reddish orange with culture age
7. Sucrose-nitrate agar slant: growth moderate, pale orange, diffusible pigment not formed
8. Glucose-asparagine agar slant: growth moderate, pale orange, diffusible pigment not formed
9. Glycerol-asparagine agar slant: growth moderate, pale orange, diffusible pigment not formed
10. Starch agar slant: growth scanty, not colored, diffusible pigment not formed
11. Tyrosine agar slant: growth moderate, pale orange, diffusible pigment not formed
12. Yeast malt agar slant: growth abundant, orange, diffusible pigment not formed
13. Oat-meal agar slant: growth moderate, pale orange, diffusible pigment not formed
14. Inorganic salts agar slant: growth scanty on inorganic salt agar containing no carbon sources, not colored, diffusible pigment not formed
15. Potato plug: growth abundant, yellowish orange to reddish orange, diffusible pigment not formed C. Physiological characteristics
1. Temperature for growth: 10°–45° C
2. Optimum temperature for growth: 25°–40° C
3. pH range for growth: 5.5–11
4. Salt tolerancy: not inhibited by 10% NaCl
5. Resistant to 0.001% Lysozyme
6. Penicillin sensitive (5 i.u. discs)
7. Nitrate reduction: positive
8. Voges-Proskauer test: negative
9. Methyl red test: negative
10. Indole production: negative
11. Hydrogen sulfide production: positive
12. Ammonia production from peptone: negative
13. Liquefaction of gelatin: negative
14. Peptonization of casein: negative
15. Litmus milk: alkaline, slight clearing with age; no coagulation
16. Hydrolysis of starch: negative
17. Hydrolysis of cellulose: negative
18. Catalase: positive
19. Cytochrome oxidase: negative
20. Urease: positive
21. Hydrolysis of DNA: negative
22. Ammonium salt, nitrate, urea are utilized as source of nitrogen
23. Acetic, n-butyric, lactic, succinic, citric, malic, L-tartaric acids assimilated
24. Cleavage of carbohydrates: Acid without gas from L-arabinose, D-xylose, D-glucose, D-fructose, D-mannose, sucrose, maltose, trehalose, glycerol, ethanol, D-sorbitol, D-mannitol, inositol; neither acid nor gas from galactose, lactose, raffinose, dextrin
25. Assimilation of various carbon sources (incubated on Pridham and Gottlieb agar and broth at 30° C for 3 weeks) L-arabinose (+), D-xylose (+), D-glucose (+), D-fructose (+), sucrose (+), inositol (+), L-rhamnose (+), raffinose (+), D-mannitol (+), ethanol (+), n-propanol (+), iso-propanol (+), n-butanol (+), propylene glycol (+), glycerol (+), propylene oxide (+), n-paraffin (+), acetamide (+), phenol (−), p-cresol (−), m-cresol (−), naphthalene (+)

D. Infrared absorption spectra of whole cells

Infrared absorption spectra of whole cells obtained by shaking culture on a glycerol Kelner-Morton medium were studied by Arai's method (J. General Applied Microbiology 9, 119 (1963)). Key absorption patterns were as follows;

Region I (2800 – 3000 $cm^{-1}$): type D,
Region II (1650 – 1750 $cm^{-1}$): type D,
Region III (1370 – 1550 $cm^{-1}$): type C,
Region IV (950 – 1250 $cm^{-1}$): type C.

II. Strain ES 3-T (FERM P-3374; ATCC 31190)

The organism has a close resemblances to strain ES 1-T except for the following characteristics: neither acid nor gas from L-arabinose, D-xylose, D-mannose, maltose.

Investigation of ES1-T and ES3-T strains by Bergey's Manual of Determinative Bacteriology, eighth edition and Waksmann, The Actinomycetes, Vol. 2 has shown that they are novel species belonging to the genus Nocardia.

*Nocardia vaccinii*, *Nocardia lutea*, *Nocardia corallina*, *Nocardia salmonicolor*, *Nocardia rubra*, and *Nocardia opaca* can be cited as species analogous to the strains in accordance with this invention. The ES1-T strain and ES3-T strain differ from *Nocardia vaccinii* and *Nocardia lutea* in regard to the growth characteristics on a nutrient agar plate, the formation of mycellium, acid-fastness, the pH range for growth, and the hydrolyzability of deoxyribonucleic acid (DNA), as shown in Table 1 to be given hereinbelow. Furthermore, as shown in Table 2, these strains differ from *Nocardia corallina* in regard to the growth characteristics on a nutrient agar plate, the optimum growth temperature, tolerancy to NaCl, the formation of acid from sucrose, and the utilization of phenol and m-cresol; and from *Nocardia salmonicolor* in regard to the growth characteristics on a nutrient agar plate, the growth characteristics on a glycerol-asparagine agar plate, the optimum growth temperature, the growth pH, tolerancy to NaCl, the formation of acid from dextrin, and the utilization of p-cresol. As shown in Table 3, the ES1-T strain and ES3-T strain further differ from *Nocardia rubra* in regard to the growth characteristics on a nutrient agar plate, the optimum growth temperature, tolerancy to NaCl, and the reduction of nitrate; and from *Nocardia*

*opaca* with regard to the growth characteristics on a nutrient agar plate, the optimum growth temperature, the growth pH and salt resistance. Since ES1-T strain and ES3-T strain grow in an inorganic salt agar culture medium, their microbiological characteristics were compared with those of *Nocardia marina* and *Nocardia atlantica* which can utilize agar as a carbon source. The results shown in Table 4 demonstrate that these strains differ from *Nocardia marina* and *Nocardia atlantica* in regard to the liquefaction of gelatin and the decomposition of cellulose.

Table 1

|  | Nocardia tartaricans nov. sp. ES1-T (FERM-P 2882; ATCC 31191) ES3-T (FERM-P 3374; ATCC 31190) | Nocardia vaccinii | Nocardia lutea |
|---|---|---|---|
| 1) Nutrient agar colonies | yellowish orange to reddish orange, capitate, smooth, entire | reddish, flat, irregular borders |  |
| 2) aerial mycelium | not formed on any tested agar slant | white | white |
| 3) acid fastness | negative | positive | partially positive |
| 4) Temperature for growth | 10 – 45° C | 10 – 35° C | 10 – 40° C |
| 5) pH range for growth | 5.5 – 11 | 6 – 9 | 6 – 10 |
| 6) Hydrolysis of DNA | negative | positive | positive |

Table 2

|  | Nocardia tartaricans nov. sp. ES1-T (FERM-P2882; ATCC 31191) ES3-T (FERM-P3374; ATCC 31190) | Nocardia corallina | Nocardia salmonicolor |
|---|---|---|---|
| 1) Nutrient agar colonies | same as in Table 1 | coral-red, raised, filamentous or arborescent margins | salmon-pink, raised, rough |
| 2) Glycerol-asparagine agar colonies | growth moderate pale orange, rhizoid |  | well developed red-orange colonies |
| 3) Temperature for growth | 10 – 45° C |  | 10 – 40° C |
| 4) Optimum temperature for growth | 25 – 40° C | 25 – 28° C | 28° C |
| 5) pH range for growth | 5.5 – 11 |  | 5 – 10 |
| 6) Salt (NaCl) tolerancy | 10% | 7% | 5% |
| 7) Cleavage of carbohydrate | no acids from dextrin; acid produced from sucrose | no acid from sucrose | acid from dextrin |
| 8) Assimilation of carbon sources | phenol, m-cresol, p-cresol are not utilized as sole carbon sources | phenol, m-cresol utilized | p-cresol utilized |

Table 3

|  | Nocardia tartaricans nov. sp. ES1-T (FERM-P 2882; ATCC 31191) ES3-T (FERM-P3374; ATCC 31190) | Nocardia rubra | Nocardia opaca |
|---|---|---|---|
| 1) Nutrient agar colonies | Same as in Table 1 | bright red, flat, rough, undulate margins | pale buff-pink, raised, rough, filamentous to entire margins |
| 2) Optimum temperature for growth | 25 – 40° C | 25 – 28° C | 30° C |
| 3) pH range for growth | 5.5 – 11 | 6 – 10 | 6 – 9 |
| 4) Salt (NaCl) tolerancy | 10% | 7% | 7% |

Table 3-continued

| | Nocardia tartaricans nov. sp. ES1-T (FERM-P 2882; ATCC 31191) ES3-T (FERM-P3374; ATCC 31190) | Nocardia rubra | Nocardia opaca |
|---|---|---|---|
| 5) Nitrate reduction | positive | negative | positive |

Table 4

| | Nocardia tartaricans nov. sp. ES1-T (FERM-P2882; ATCC 31191) ES3-T (FERM-P3374; ATCC 31190) | Nocardia marina | Nocardia atlantica |
|---|---|---|---|
| 1) Nutrient agar colonies | Same as in Table 1 | bright lemon-yellow, flat, smooth, undulate margins | yellow to orange-yellow |
| 2) Gelatin liquefaction | negative | positive | positive |
| 3) Nitrate reduction | positive | negative | positive |
| 4) Hydrolysis of cellulose | negative | positive | positive |
| 5) Hydrolysis of starch | negative | positive | negative |

On the basis of the above examination, ES1-T strain and ES3-T strain have been identified as novel strains belonging to the genus Nocardia, and termed *Nocardia tartaricans* nov. sp.

According to the process of this invention, a microorganism of the genus Nocardia, preferably *Nocardia tartaricans* nov. sp., having the ability to produce cis-epoxysuccinate hydrolase, or an enzyme isolated from said microorganism is contacted with cis-epoxysuccinic acid or its derivatives in an aqueous medium.

The cis-epoxysuccinate hydrolase used in this invention is obtained by cultivating the above microorganism in a customary manner. The cultivation of the above microorganism is carried out usually in an aqueous medium. It can also be carried out on a solid surface. Natural culture media such as nutrient broth and synthetic culture media composed of a suitable carbon source such as glucose, sucrose, glycerol, ethanol, isopropanol or n-paraffin, a suitable nitrogen source such as ammonium salts, nitric acid salts and urea and other inorganic salts can be used for the cultivation. It is desirable to add cis-epoxysuccinic acid or its derivatives to the culture medium for inducing the required enzyme.

The pH of the culture medium is adjusted to 5.5 to 11, preferably about 6 – 10. The cultivation is carried out aerobically at about 10 to about 45° C, preferably about 25° to about 40° C. In batchwise operations, the cultivation is carried out usually for half a day to 10 days.

In the performance of the process of this invention, the contacting of the microorganism having the ability to produce cis-epoxysuccinate hydrolase or an enzyme isolated therefrom with cis-epoxysuccinic acid or its derivatives can be effected in various modes. For example, the contacting can be carried out while the microorganism is in the form of growing culture, culture broth, living cells, dried cells, pulverized cells or cell extract. It can also be in the form of purified enzyme by employing a purifying means.

Figure 1:
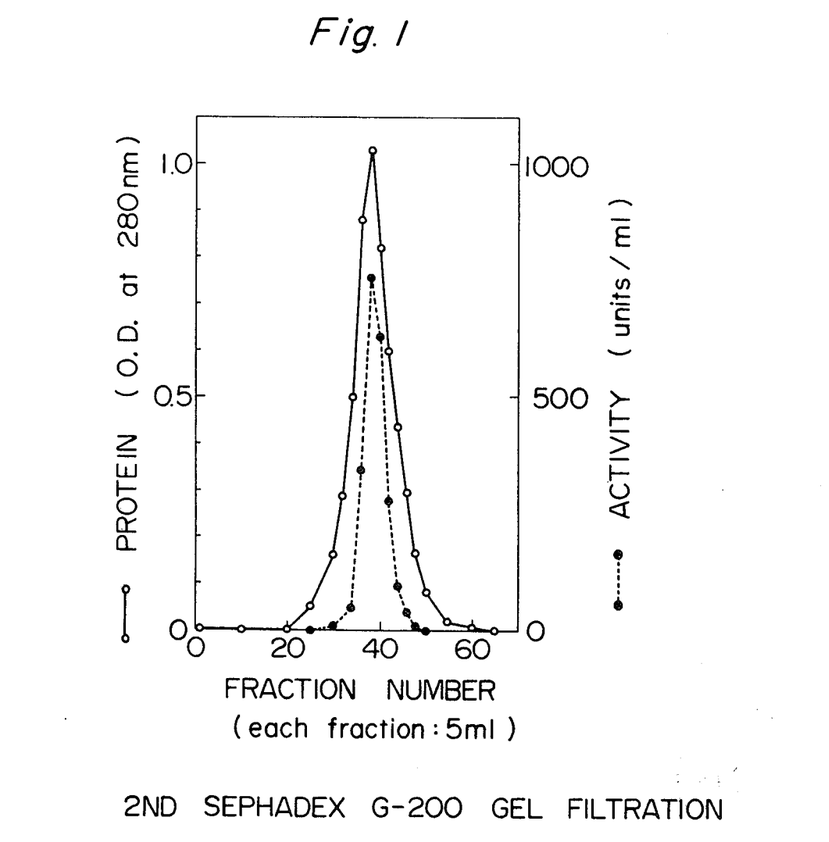

When the enzyme is used in a purified form, the following procedure can be applied to the isolation and purification of the enzyme. Cells harvested from a culture broth by centrifugation are suspended in a 0.05M phosphate buffer (pH 7) and destroyed by sonic oscillation. The crude cell-free extract thus obtained is fractionated by precipitation with ammonium sulfate and a fraction of 50 to 60% saturation is collected. The precipitate is dissolved in a small volume of 0.05M phosphate buffer (pH 7) and dialyzed against a large volume of the same buffer and then purified by DEAE-Sephadex A-50 column chromatography and gel filtration with a Sephadex G-200 column.

cis-Epoxysuccinate hydrolase isolated from *Nocardia tartaricans* nov. sp. ES3-T (FERM P-3374; ATCC 31190) and purified by the procedure described above has the following properties. (The elution pattern of the 2nd gel filtration of Sephadex G 200 is shown in FIG. 1.)

1. Catalytic action: hydrolyzes cis-epoxysuccinate, producing L(+)-tartaric acid.
2. Molecular weight: 60,000 – 95,000 by the Andrews method.
3. Substrate specificity: does not hydrolyze d- or l-trans-epoxysuccinate.
4. Optimum pH: 8 – 9
5. Optimum temperature: 50° C in 20–80 minutes' incubation, and 45° C in several hours' incubation
6. pH stability: stable at pH 7.0, unstable at pH below 5.0 and pH over 10.0.
7. Temperature stability: stable at temperatures below 40° C in 10-minute incubation at pH 7.0; lost activity at temperatures higher than 60° C in 10-minute incubation at pH 7.0.
8. Inhibitors and activators: summarized in Table 5 below

Table 5

| Inhibitors and activators | mM | Remaining activity (%) |
|---|---|---|
| None | — | 100 |
| EDTA | 1 | 88 |
|  | 10 | 84 |
| α,α'-Dipyridyl | 1 | 88 |
| o-Phenanthroline | 1 | 39 |
| Ammonium oxalate | 1 | 45 |
| Mercaptoethanol | 10 | 109 |
| p-Chloromercuribenzoate | 1 | 89 |
| Iodoacetamide | 1 | 86 |
| $MgSO_4 \cdot 7H_2O$ | 1 | 106 |
| $FeSO_4 \cdot 7H_2O$ | 1 | 115 |
| $ZnSO_4 \cdot 7H_2O$ | 1 | 55 |
| $CuCl_2 \cdot 2H_2O$ | 1 | 56 |
| $NiCl_2$ | 1 | 86 |
| $CoCl_2$ | 1 | 56 |
| $CaCl_2 \cdot 2H_2O$ | 1 | 111 |
| Fumarate | 10 | 90 |
| dl-trans-Epoxysuccinate | 100 | 126 |

The optimum pH (4), the optimum temperature (5), the pH stability (6), and the temperature stability (7) above are shown in FIGS. 2, 3, 4 and 5. In these figures, TA is an abbreviation for L-tartaric acid, and ESA, for cis-epoxysuccinic acid.

The enzymatic activity, the quantity of tartaric acid and the quantity of protein employed in the determination of the enzymatic properties of cis-epoxysuccinate hydrolase used in this invention were measured by the following methods.

1. Measurement of enzymatic activity 1.0 ml of 1M ESA·Na$_2$ was added to 3.9 ml of a 0.1M phosphate buffer (pH 8.0), and the mixture was maintained at 37° C for 5 minutes. Then, 0.1 ml of an enzyme solution was added, and the mixture allowed to stand for 20 minutes at 37° C. The quantity of tartaric acid formed in the resulting reaction mixture was determined. The amount of the enzyme which forms 1 μmole of tartaric acid per hour under the above-mentioned reaction conditions is defined as one unit, and the number of such units per mg of protein is defined as specific activity.

2. Determination of the quantity of tartaric acid

An enzyme reaction solution was added to 1 ml of 2% ammonium metavanadate reagent, and the mixture was diluted to 4 ml. with water. Then, 1 ml of 1N sulfuric acid was added, and after a lapse of 30 minutes, the absorbance of the solution at 530 nm was measured.

3. Determination of the quantity of protein

The quantity of protein was determined from the absorbance at 280 nm, setting $E_{1\,cm}^{1\%}$ at 15.

The cis-epoxysuccinate hydrolase in accordance with this invention differs from the conventional enzymes disclosed in Japanese Laid-Open Patent Publication No. 140684/75 and others cited above which are produced by microorganisms belonging to the genus Achromobacter or genus Alcaligenes used to produce L-tartaric acid from cis-epoxysuccinic acid. For example, the prior patent states that the conventional enzymes have a molecular weight of about 25,000 to about 45,000. But the cis-epoxysuccinate hydrolase in accordance with this invention has a molecular weight of about 60,000 to about 95,000. Furthermore, while the optimum pH for the conventional enzymes is 7 to 8, it is 8 to 9 with the cis-epoxysuccinate hydrolase of this invention. The optimum temperature is 57° C for 1-hour incubation and 50° to 52° C for 3-hour incubation for the conventional enzymes, but 50° C for 1-hour incubation and 45° C for 3-hour incubation for the cis-epoxysuccinate hydrolase of this invention.

According to the process of this invention, the contacting of a microorganism having the ability to produce the cis-epoxysuccinate hydrolase or an enzyme isolated therefrom with cis-eposysuccinic acid or its derivatives in an aqueous medium is carried out in the absence of a surface active agent.

The reaction can be carried out by a batch method, a continuous method, or a semi-batch method in which the substrate and other required materials are successively fed during the reaction. It is also possible to employ a flow reaction technique in which the microorganism or the enzyme is fixed to a suitable support and packed in a column. The reaction can be carried out at a temperature of about 20 to about 60° C., preferably about 25° to about 45° C at a pH of about 5 to about 10, preferably about 6 to about 10, more preferably about 7 to about 9.

In one embodiment of this invention, cis-epoxysuccinic acid or its derivatives can be added either partly or wholly to the liquid culture medium, and then the above-specified microorganism cultivated in it to build up L-tartaric acid in the culture broth.

L-tartaric acid can be recovered from the reaction mixture, for example, by removing the cells by centrifugal separation and concentrating the filtrate. Another recovering procedure comprises adding a calcium salt to precipitate the product as calcium tartrate tetrahydrate, separating the L-tartrate by filtration or any other desired solid-liquid separating means, and converting it to L-tartaric acid in a conventional manner. The resulting L-tartaric acid has been identified as the same as natural tartaric acid by its Rf value in paperchromatography, its degree of migration in filter paper electrophoresis and also its IR spectrum, NMR spectrum, degree of rotation and elemental analysis values.

The following Examples illustrate the present invention in greater detail.

EXAMPLE 1

Each 500 ml. shaking flask was charged with 50 ml. of a culture medium (pH 7.0) containing 1% of meat extract, 1% of peptone and 0.3% of sodium chloride, and the culture medium was sterilized at 121° C for 15 minutes. Sterilized sodium cis-epoxysuccinate was added in a concentration of 1% to the culture medium, and *Nocardia tartaricans* nov. sp. (Strain ES1-T: FERM P-2882: ATCC 31191) was inoculated, and cultivated shakingly at 30° C for 24 hours. The cell concentration was 3.5 g/liter. The cells were separated centrifugally from the resulting culture broth, washed once with a physiological saline solution and further centrifuged to collect the resulting cells.

The collected cells, 25 mg as a dry weight, were added to 25 ml. of a 1 mole/l aqueous solution of sodium cis-epoxysuccinate (pH 7.0), and the reaction was carried out at 30° C. The results are shown in Table 6.

Table 6

| Time (hours) | Amount of tartaric acid formed (g/l) | Yield of tartaric acid (%) |
|---|---|---|
| 24 | 39.5 | 26.3 |
| 48 | 90.0 | 60.0 |
| 72 | 139.1 | 92.7 |

Table 6-continued

| Time (hours) | Amount of tartaric acid formed (g/l) | Yield of tartaric acid (%) |
| --- | --- | --- |
| 90 | 145.7 | 97.1 |

The maximum rate of tartaric acid formation was 2.04 g/l.hr which was 2.04 g/g of cell per hour. This corresponded to 47.6 units as the enzymatic activity of 1 ml. of the original culture broth.

EXAMPLE 2

A 10-liter jar fermentor was charged with 5 liters of a culture medium having the following composition.

| | |
| --- | --- |
| Propylene glycol | 1.5% |
| Urea | 0.3% |
| $KH_2PO_4$ | 0.2% |
| $Na_2HPO_4$ | 0.2% |
| $MgSO_4 \cdot 7H_2O$ | 0.1% |
| $FeSO_4 \cdot 7H_2O$ | 0.001% |
| $CaCl_2 \cdot 2H_2O$ | 0.003% |
| $MnSO_4 \cdot 4H_2O$ | 0.0004% |
| $ZnSO_4 \cdot 7H_2O$ | 0.0001% |
| $Co(NO_3)_2 \cdot 6H_2O$ | 0.00001% |
| Yeast extract | 0.05% |
| pH | 7.0 |

The above culture medium was prepared as follows: A culture medium containing the above ingredients except urea was sterilized at 121° C for 15 minutes, and a separately prepared urea solution filtered and sterilized was added. The pH of the mixture was adjusted with sodium hydroxide and hydrochloric acid to afford the culture medium finally having the above-mentioned composition and pH.

*Nocardia tartaricans* nov. sp. (strain ES-3T: FERM P-3374: ATCC 31190) was inoculated in this culture medium, and cultivated at 30° C for 48 hours while passing air at a rate of 5 liters/min. (1 v.v. m) and adjusting the speed of stirring to 600 rpm. The final cell concentration was 5.3 g/l. After the cultivation, 300 ml. of the culture broth was taken, and the cells were collected by centrifugal separation. The cells were suspended in 300 ml. of a culture medium of the same composition as above except that 0.2 mol/l of sodium cis-epoxysuccinate was used and propylene glycol was omitted. The suspension was maintained at 30° C. for 20 hours to induce an enzyme. To 5 ml. of this solution was added 5 ml. of a 1 mol/l solution of sodium cis-epoxysuccinate, and the reaction was carried out at 37° C. 5 ml. of a 2 mol/l solution of sodium cis-epoxysuccinate was added successively at the end of 4 hours, 22 hours and 45 hours, respectively. The results are shown in Table 7.

Table 7

| Reaction time (hours) | 4 | 22 | 45 | 67 |
| --- | --- | --- | --- | --- |
| Amount of the reaction mixture (ml) | 10 | 15 | 20 | 25 |
| Concentration of tartaric acid (mg/ml) | 20.8 | 95.4 | 143 | 212 |
| Amount of tartaric acid formed (mg) | 208 | 1431 | 2860 | 5300 |
| Amount of tartaric acid formed (m-mol) | 1.39 | 9.54 | 19.1 | 35.3 |
| Activity (units/ml-broth) | 69.5 | 90.6 | 83.1 | 135 |

The activity shown in the last row of Table 8 is an average activity per ml of the original culture broth for each reaction period of 0 to 4 hours, 4 to 22 hours, 22 to 45 hours, and 45 to 69 hours.

EXAMPLE 3

*Nocardia tartaricans* nov. sp. (strain ES-3T, FERM P-3374; ATCC 31190) was cultivated in a 10-liter jar fermentor at 30° C for 48 hours. The composition of the medium is as follows; propylene glycol 1%, urea 0.3%, $KH_2PO_4$ 0.2%, $Na_2HPO_4$ 0.2%, $MgSO_4 \cdot 7H_2O$ 0.1%, $FeSO_4 \cdot 7H_2O$ 0.001%, $CaCl_2 \cdot 2H_2O$ 0.003%, $MnSO_4 \cdot 4H_2O$ 0.0004%, yeast extract 0.05% (pH 7.0). cis-Epoxysuccinate (0.5%) was added at logarithmic growth phase. The cells were harvested and destroyed by ultrasonic oscillation. The resulting crude cell-free extract contained 11300 mg of protein, and had a total enzymatic activity of 200,000 units. The crude cell-free extract was treated with streptomycin sulfate and the mixture was centrifuged. The supernatant was fractionated with ammonium sulfate and a fraction of 50 to 60% saturation was collected. This fraction was dialyzed against a 0.05 mol/l phosphate buffer at a pH of 7.0 which contained $5 \times 10^{-3}$ mol/l of mercaptoethanol, and charged into a column of DEAE Sephadex A-50 previously equilibrated with the same buffer. The column was washed with the equilibrating buffer. The enzyme was eluted with a 0.05 mol/l phosphate buffer (pH 7.0) which contained 0.3 mol/l NaCl and $5 \times 10^{-3}$ mol/l mercaptoethanol. Active fractions were collected. Their total volume was 1250 ml. These fractions contained 832 mg of protein and had a total enzymatic activity of 65,400 units. This enzyme solution was concentrated by ammonium sulfate precipitation.

The precipitate was dissolved in a small volume of a 0.05 mol/l phosphate buffer and dialyzed against the same buffer. The dialyzate was fractionated with ammonium sulfate. A fraction of 50 to 55% saturation was collected and then subjected to gel filtration on Sephadex G-200. The enzyme was eluted with a 0.05 mol/l phosphate buffer (pH 7.0).

Active fractions were collected and concentrated by ammonium sulfate precipitation. The precipitate was dissolved in a small volume of phosphate buffer and again subjected to Sephadex G-200 in the same manner as described before.

FIG. 1 of the accompanying drawings shows an elution pattern of the second gel filtration on Sephadex G-200. Fractions of 36 to 42 were collected until their total volume became 37.0 ml. This purified enzyme solution contained 19.9 mg of protein and had a total enzymatic activity of 18,000 units.

A mixture consisting of 0.4 ml. of the purified enzyme solution so obtained, 7.6 ml. of a 0.05 mol/l tris-HCl buffer (pH 8.5) and 2.0 ml. of 2 mol/l sodium cis-epoxysuccinate was incubated at 37° C for 16 hours. 615 mg of L(+)-tartaric acid was formed in a yield of 100% in the resulting reaction mixture.

EXAMPLE 4

*Nocardia tartaricans* nov. sp. (strain ES-3T. FERM P-3374; ATCC 31190) was cultivated in a 10-liter jar fermentor containing the same medium as described in Example 3 at 30° C for 48 hours. After an ultrasonic oscillation treatment the crude cell-free extract was mixed with DEAE-Sephadex A-50 previously equilibrated with a 0.05 mol/l phosphate buffer containing $5.0 \times 10^{-3}$ mol/l mercaptoethanol. This DEAE-Sephadex was packed into a column (6.0 × 53 cm). The column was washed with the equilibrating buffer and then the enzyme was eluted with the same buffer containing 0.3 mol/l NaCl. Fractions of 10 to 20 were collected and concentrated by ammonium sulfate precipitation. The precipitate was dialyzed against a 0.05M phosphate buffer. The dialyzate was centrifuged to give 150 ml. of a supernatant which contained 970 mg of protein and had a total enzymatic activity of 121,200 units.

A mixture consisting of 10 ml. of this enzyme solution, 50 ml. of distilled water and 50 ml of 2 mol/l sodium cis-epoxysuccinate whose pH was adjusted to 8.5 with 4N sodium hydroxide was incubated at 37° C for 15 hours with mild stirring. 15.1 g of L(+)-tartaric acid was formed in a yield of 100% in the resulting reaction mixture.

Figure 2:
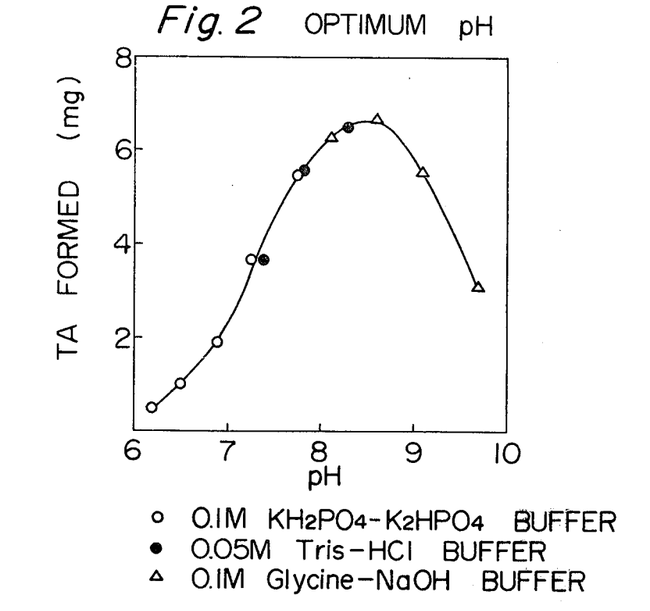
Figure 3:
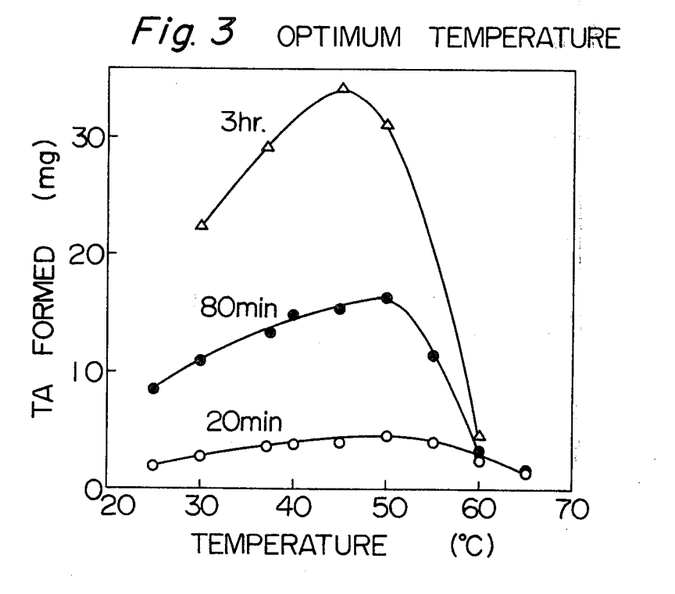

What we claim is:

1. Cis-epoxysuccinate hydrolase obtained from *Nocardia tartaricans* characterized by (1) a molecular weight of from 60,000 to 95,000, (2) an optimum pH as illustrated in FIG. 2, (3) an optimum temperature as illustrated in FIG. 3, (4) a pH stability as illustrated in FIG. 4, and (5) a temperature stability as illustrated in FIG. 5.

2. A method of producing the enzyme cis-epoxysuccinate hydrolase which comprises culturing a microorganism belonging to the species *Nocardia tartaricans* capable of producing said enzyme in a nutrient medium containing assimilable sources of carbon and nitrogen until a microbial population is developed; harvesting said microbial cells and thereafter isolating said enzyme therefrom.

3. A method according to claim 2 wherein said microorganism is *Nocardia tartaricans* nov. sp. ATCC 31190.

4. A method according to claim 2 wherein said microorganism is *Nocardia tartaricans* nov. sp. ATCC 31191.

5. A method according to claim 2 wherein said enzyme is isolated by disrupting said microbial cells to obtain a crude cell-free extract; fractionating said extract by precipitation with ammonium sulfate; dialyzing said precipitate and then purifying by column chromatography and gel filtration.

6. A method for preparing L-tartaric acid which comprises reacting cells of a microorganism belonging to the genus Nocardia having the ability to produce an enzyme which hydrolyzes the epoxy ring of cis-epoxysuccinic acid or cis-epoxysuccinic hydrolase derived from said microorganism with cis-epoxysuccinic acid or a derivative thereof having the cis-epoxysuccinic acid structure in an aqueous medium, and thereafter recovering L-tartaric acid from said aqueous medium.

7. A method according to claim 6 wherein said microorganism belongs to the species *Nocardia tartaricans*.

8. A method according to claim 7 wherein said microorganism is selected from the group consisting of *Nocardia tartaricans* nov. sp. ATCC 31190 and *Nocardia tartaricans* nov. sp. ATCC 31191.

9. A method according to claim 6 wherein said reaction step is carried out at a temperature of from about 20° C. to about 60° C.

10. A method according to claim 6 wherein said reaction step is carried out at a pH of about 6 to about 10.

11. A method according to claim 6 wherein said reaction step is carried out by culturing said microorganism in said aqueous medium.

12. A method according to claim 6 wherein said reaction step is carried out using a culture broth or a cell free extract containing said cis-epoxysuccinate hydrolase.

13. A method according to claim 6 wherein said reaction step is carried out using dried or pulverized cells of said microorganism.

14. A method for preparing L-tartaric acid which comprises culturing a microorganism belonging to the genus Nocardia having the ability to produce an enzyme which hydrolyzes the epoxy ring of cis-epoxysuccinic acid in an aqueous medium containing cis-epoxysuccinic acid or a derivative thereof having the cis-epoxysuccinic acid structure until L-tartaric acid is formed in said medium and thereafter recovering said L-tartaric acid.

15. A method according to claim 14 wherein said microorganism is selected from the group consisting of *Nocardia tartaricans* nov. sp. ATCC 31190 and *Nocardia tartaricans* nov. sp. ATCC 31191.

* * * * *